United States Patent
Hood et al.

(10) Patent No.: US 8,292,864 B2
(45) Date of Patent: Oct. 23, 2012

(54) ABSORBENT ARTICLE HAVING A MULTILAYER VISUAL SIGNAL

(75) Inventors: Lisa June Hood, Cincinnati, OH (US); David Christopher Oetjen, West Chester, OH (US); Signe Christina Larson, Cincinnati, OH (US); John Lee Hammons, Hamilton, OH (US)

(73) Assignee: The Procter and Gamble Company, Cincinnati, OH (US)

( * ) Notice: Subject to any disclaimer, the term of this patent is extended or adjusted under 35 U.S.C. 154(b) by 481 days.

(21) Appl. No.: 12/548,604

(22) Filed: Aug. 27, 2009

(65) Prior Publication Data
US 2010/0036352 A1    Feb. 11, 2010

Related U.S. Application Data

(63) Continuation-in-part of application No. 12/188,543, filed on Aug. 8, 2008, now Pat. No. 7,967,801, and a continuation-in-part of application No. 12/188,598, filed on Aug. 8, 2008, now Pat. No. 8,058,501.

(51) Int. Cl.
*A61F 13/15* (2006.01)
*A61F 13/20* (2006.01)
(52) U.S. Cl. ......... 604/385.11; 604/385.101; 604/378
(58) Field of Classification Search ........... 604/385.01, 604/378, 385.101
See application file for complete search history.

(56) References Cited

U.S. PATENT DOCUMENTS

| | | | |
|---|---|---|---|
| 4,673,403 A | 6/1987 | Lassen et al. | |
| 5,647,863 A * | 7/1997 | Hammons et al. | 604/378 |
| 2003/0078553 A1 | 4/2003 | Wada et al. | |
| 2004/0170813 A1 * | 9/2004 | Digiacomantonio et al. | 428/195.1 |
| 2005/0154365 A1 * | 7/2005 | Zander et al. | 604/385.04 |
| 2006/0025735 A1 * | 2/2006 | Berg et al. | 604/385.01 |
| 2006/0025736 A1 * | 2/2006 | Berg et al. | 604/385.01 |
| 2006/0129115 A1 | 6/2006 | Visscher et al. | |
| 2007/0087169 A1 | 4/2007 | McFall | |
| 2007/0293834 A1 * | 12/2007 | Miura et al. | 604/385.01 |
| 2008/0208153 A1 | 8/2008 | Oetjen et al. | |
| 2009/0030390 A1 | 1/2009 | Hammons et al. | |
| 2009/0281513 A1 * | 11/2009 | Nelson | 604/379 |

OTHER PUBLICATIONS

PCT International Search Report dated Jun. 14, 2010.

* cited by examiner

*Primary Examiner* — Tatyana Zalukaeva
*Assistant Examiner* — Ginger T Chapman
(74) *Attorney, Agent, or Firm* — Megan C. Hymore; Andrew J. Hagerty; Gary J. Foose

(57) ABSTRACT

An absorbent article and method of making an absorbent article. The absorbent article has a first layer and a second layer in facing relationship with one another. The first layer has a first imparted colored region coincident with the longitudinal centerline. The second layer has a second imparted colored region laterally more extensive in a direction orthogonally away from the longitudinal centerline than the first imparted colored region. The second imparted colored region extends across the longitudinal centerline and has free ends. The absorbent article has a background region. The first imparted colored region and the second imparted colored region differ in color as compared to the background region.

5 Claims, 4 Drawing Sheets

ABSORBENT ARTICLE HAVING A MULTILAYER VISUAL SIGNAL

CROSS REFERENCE TO RELATED APPLICATION

This application is a continuation-in-part of application Ser. No. 12/188,543, filed Aug. 8, 2008 now U.S. Pat. No. 7,967,801. This application is a continuation-in-part of application Ser. No. 12/188,598, filed Aug. 8, 2008 now U.S. Pat. No. 8,058,501.

FIELD OF THE INVENTION

Disclosed is an absorbent article having visually perceptible elements on multiple layers of the absorbent article.

BACKGROUND OF THE INVENTION

A variety of absorbent articles that include different colored regions are available in the market. Absorbent articles such as sanitary napkins and female adult incontinence articles that function to collect fluid discharged from a woman's vagina or urethra sometimes include a colored region proximal the central portion of the absorbent article that differs in color from portions of the absorbent article remote from the central portion of the absorbent article.

By including a colored region in the central portion of the absorbent article, manufacturers of absorbent articles have effectively taught consumers that the central portion of the absorbent article is where the fluid collected should reside. Manufacturers have devised a variety of designs for central colored regions. In some absorbent articles, the central colored region is relatively narrow as compared to the overall width of the absorbent article and extends only along about one-half of the length of the absorbent article. One possible reason that relatively narrow central colored regions were adopted was that such colored regions could provide a desired visual impression, such as the impression of depth. Central colored regions also might help the consumer understand how her use and placement of the product in her panty might be affecting the staining pattern of absorbent article, which might help her improve how and where she mounts the chassis of the absorbent article in her panty to achieve maximum performance. Manufacturers that have adopted designs having narrow central colored regions have developed manufacturing capability and capacity to produce absorbent articles having such designs at high speed.

High speed manufacturing lines that include printing capability represent a high capital cost to manufacturers of absorbent articles. For manufacturers to effectively recover the cost of such capital, it is advantageous for manufacturers to use existing manufacturing lines to continue manufacturing absorbent articles. In some instances, the approach manufacturers have chosen to provide for central colored regions might not be easily adapted to provide for colored regions that are wider than those formerly produced, due to the crowded nature of the manufacturing line. Thus, if a manufacturer desires to provide for visual elements across a greater width of the absorbent article, the manufacturer might have to retool the manufacturing line to provide for more laterally extensive colored regions, thus incurring additional capital cost.

Another problem associated with narrow central colored regions on absorbent articles is that some consumers associate stain patterns that extend outside the central colored region as indicating that the absorbent capacity of the absorbent article is exhausted. In some absorbent articles, the central colored region could account for less than 25% of the absorbent capacity of the absorbent article.

Absorbent articles currently available in the market place are generally provided with colored regions on only a single component, such as the secondary topsheet or topsheet. Such an approach limits the design space in which designers can create innovative designs that meet consumer demands and might limit the ability of manufacturers to easily move to more complex and laterally extensive designs.

With these limitations in mind, there is a continuing unaddressed need for absorbent articles that can be manufactured cost effectively using existing manufacturing capability that can be provided with additional colored regions that are laterally more extensive than those formerly produced by such manufacturing lines. Further, there is a continuing unaddressed need for absorbent articles that reassure the user that fluid in the absorbent article in regions outside of a relatively narrow colored region is securely retained in the absorbent article and she need not worry about a leak. Further, there is a continuing unaddressed need for absorbent articles that are provided with colored regions on multiple layers so that designers have a richer palette of color impression with which to work.

SUMMARY OF THE INVENTION

Disclosed is an absorbent article having a body facing surface and a garment facing surface. The absorbent article comprises a first layer and a second layer in facing relationship with one another. The absorbent article has a centroid. The absorbent article has a longitudinal centerline and a transverse centerline intersecting the longitudinal centerline at the centroid and, the transverse centerline is orthogonal to the longitudinal centerline. The absorbent article has a background region. The first layer comprises a first imparted colored region coincident with the longitudinal centerline. The second layer comprises a second imparted colored region laterally more extensive in a direction orthogonally away from the longitudinal centerline than the first imparted colored region. The second imparted colored region extends across the longitudinal centerline. The second imparted colored region has free ends. The background region, first imparted colored region, and the second imparted colored region are viewable from the body facing surface. The first imparted colored region and the second imparted colored region differ in color from the background region.

Also disclosed is a method for fabricating an absorbent article having a body facing surface, a garment facing surface, and a periphery. The absorbent article comprises a first layer and a second layer in facing relationship with one another. The absorbent article has a centroid. The absorbent article has a longitudinal centerline and a transverse centerline intersecting the longitudinal centerline at the centroid and orthogonal to the longitudinal centerline. The method comprises the steps of providing the first layer with a first imparted colored region coincident with the longitudinal centerline. The first imparted colored region is provided by a first coloration technique. The second layer is provided with a second imparted colored region that is laterally more extensive in a direction orthogonally away from the longitudinal centerline than the first imparted colored region and extends across the longitudinal centerline. The second imparted colored region extends across the longitudinal centerline. The second imparted colored region is provided by a second coloration technique. The first layer and second layer are brought into registration with one another. The absorbent article comprises a background region. The background region, the first imparted colored region, and the second imparted colored region are viewable from the body facing surface. The first imparted colored region and the second imparted colored region differ in color from the background region.

DETAILED DESCRIPTION OF THE INVENTION

"Absorbent articles" as referred to herein can be sanitary napkins, pantiliners, or incontinence pads that are worn in the crotch region of an undergarment. It is even conceivable that baby diapers, adult incontinence diapers, and human waste management devices might benefit from the present invention even though they are conventionally not worn in conjunction with an undergarment. Absorbent articles can be disposable absorbent articles.

The term 'color' as referred to herein includes any primary color, i.e., white, black, red, blue, violet, orange, yellow, green, and indigo as well as any declination thereof or mixture thereof. The term 'non-color' or 'non-colored' refers to the color white which is further defined as those colors having an L* value of at least 80, an a* value equal to 0±2, and a b* value equal to 0±2.

The term 'disposable' is used herein to describe absorbent articles that are not intended to be re-launched or otherwise restored or reused as an absorbent article (i.e., they are intended to be disposed of after a single use).

Non-limiting examples of panty liners and sanitary napkins which may be provided with a first imparted colored region on a first layer and second imparted colored region on a second layer include those manufactured by The Procter & Gamble Company of Cincinnati, Ohio, such as ALWAYS ULTRA, ALWAYS INFINITY, and ALWAYS pantiliners. Absorbent articles such as those disclosed in U.S. Pat. Nos. 4,324,246, 4,463,045, 6,004,893, 4,342,314, 4,463,045, 4,556,146, 4,589,876, 4,687,478, 4,950,264, 5,009,653, 5,267,992, and Re. 32,649 are also contemplated as being absorbent articles that might benefit from such a structure.

Figure 1:
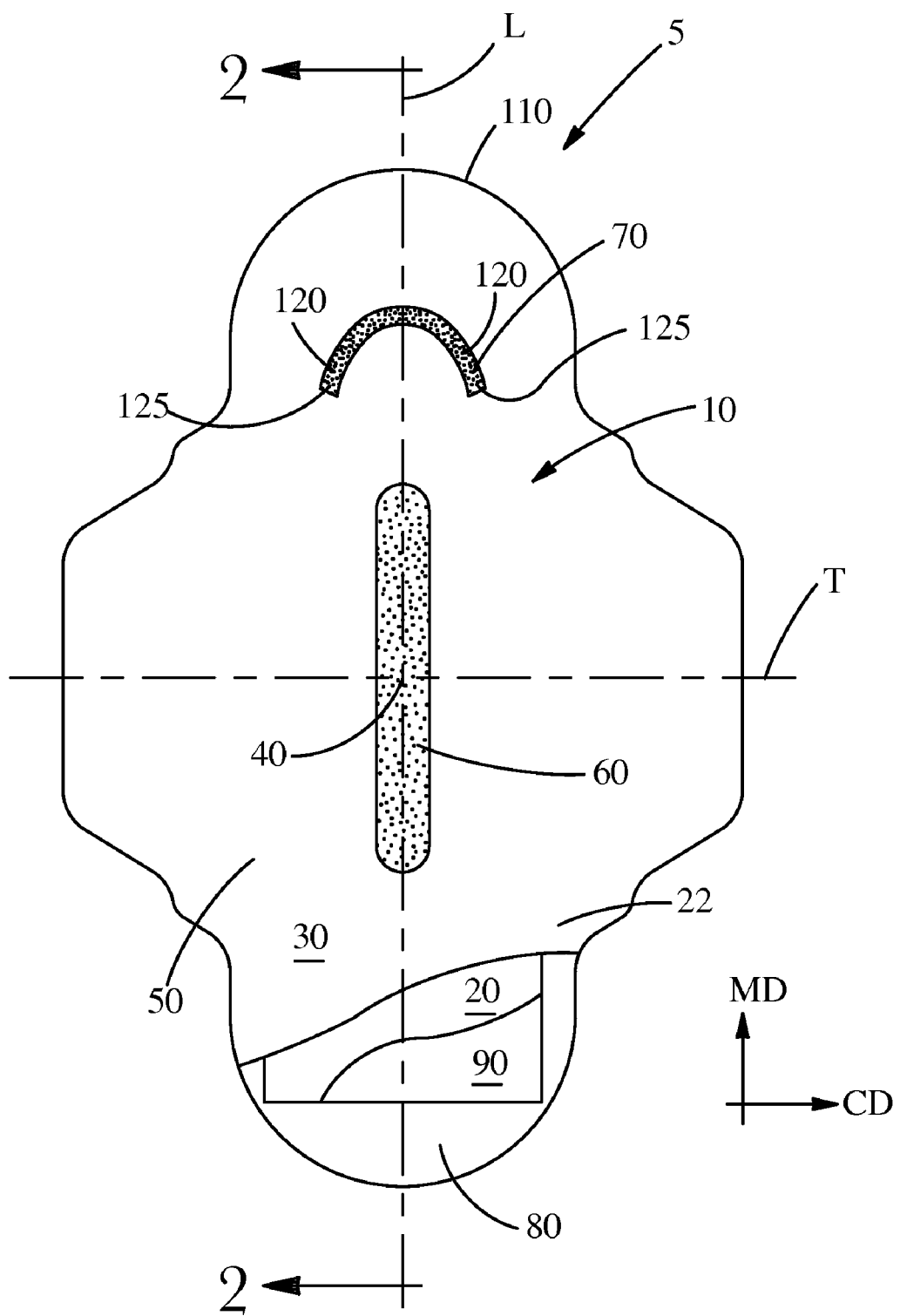
FIG. 1 is a schematic of an absorbent article.

A top view of an absorbent article 5 is shown in FIG. 1. The absorbent article 5 can have a substantially planar configuration and a centroid 40. The centroid 40 is the in-plane center of mass of the absorbent article 5. The centroid 40 is at the intersection between the longitudinal centerline L and transverse centerline T. The transverse centerline T is orthogonal to the longitudinal centerline L. The absorbent article 5 need not be symmetric about the transverse centerline T. The absorbent article 5 can be symmetric about the transverse centerline T. The absorbent article 5 has a body facing surface 10 and a garment facing surface. The absorbent article 5 comprises a first layer 20 and a second layer 22. The first layer 20 and second layer 22 can be in a facing relationship. For example first layer 20 and second layer 22 can be substantially planar webs of material overlying one another and in contact with one another or overlying one another with another material or web of material (or more than one material/web of material) intermediate between the first layer 20 and second layer 22. The absorbent article can have a backsheet 80. The second layer 22 can be the topsheet 30.

As shown in FIG. 1, the absorbent article 5, can be considered to have a viewing surface that is the body facing surface 10. The body facing surface 10 can be the side of the absorbent article 5 that is in contact the wearer's body when the absorbent article 5 is worn, as might be the case for a sanitary napkin, panti-liner, or adult incontinence product, or is inserted into the wearer's body, as might be the case for a tampon. For a generally cylindrical tampon, the longitudinal centerline L is considered to be on the body facing surface 10 of the tampon, aligned with the central axis of the tampon and the centroid 40 can be the midpoint of the longitudinal centerline L.

The body facing surface 10 can be the side of the second layer 22 that is in contact the wearer's body when the absorbent article 5 is worn. In such an arrangement, the second layer 22 can function as a topsheet, the second layer 22 being a fluid pervious polymer film, fluid pervious nonwoven, or other suitably fluid pervious material. In another embodiment, a topsheet, such as a fluid pervious polymer film or fluid pervious nonwoven, can be between the wearer's body and the second layer 22. The first layer 20 and second layer 22 are visible (can be visually perceived by the observer) when the body facing surface 10 is presented towards an observer even though the second layer 22 is between the observer and the first layer 20.

When the body facing surface 10 of the absorbent article 5 is viewed, the absorbent article 5 can have a background region 50. The background region 50 is a region that is visually distinguishable from the first imparted colored region 60 and second imparted colored region 70. The background region 50 can be white or any other color visually distinguishable from the first imparted colored region 60 and second imparted colored region 70. Colors are believed to be visually distinguishable if there is a ΔE between the two colors of at least about 1.

The first layer 20 comprises the first imparted colored region 60. The first imparted colored region 60 can be a constituent part of first layer 20, as might be the case if a predetermined portion of first layer 20 comprises pigmented fibers or has been rendered to have a color that differs from the constituent color of first layer 20. The first imparted colored region 60 can be provided by printing on a portion the first layer 20. The first imparted colored region 60 can be the constituent color of the first layer 20 with the background region 50 rendered to have a color that differs from the constituent color of the first layer 20. The first imparted colored region 60 can be provided on, for instance, the body facing side of the first layer 20 or the garment facing side of the first layer 20, the garment facing side of a layer or the absorbent article 5 being the side of the layer or absorbent article 5 oriented away from the wearer's body. The body facing side of the first layer 20 is oriented towards the second layer 22.

Similarly, the second layer 22 comprises the second imparted colored region 70. The second imparted colored region 70 can be a constituent part of the second layer 22, such as a predetermined portion of second layer 22 that comprises pigmented fibers or has been rendered to have a color than differs from the constituent color of the second layer 22, for example by printing. The second imparted colored region 70 can be the constituent color of the second layer 22 with the background region 50 rendered to have a color that differs from the constituent color of the second layer 22. The second imparted colored region 70 can be provided on, for instance, the body facing side of the second layer 22 or the garment facing side of the second layer 22, the garment facing side of the second layer 22 being the side of the absorbent article oriented away from the wearer's body and towards the first layer 20. Providing the first imparted colored region 60 and the second imparted colored region 70 on two different layers of material may provide for a manufacturing approach that might not require significant alteration of the manufacturing line to produce the desired absorbent article 5.

The first imparted colored region 60 can be coincident with the longitudinal centerline L. That is, a portion of the first imparted colored region 60 can intersect with the longitudinal centerline L.

When the body facing surface 10 is viewed, the background region 50, first imparted colored region 60, and second imparted colored region 70 are viewable by an observer. The first imparted colored region 60 and second imparted colored region 70 are visibly distinct from the background region 50 in that first imparted colored region 60 and second imparted colored region 70 each differ in color as compared to the background region 50. The first imparted colored region 60 and the background region 50 can differ in color by a ΔE, which is discussed in more detail below, of at least about 1. The first imparted colored region 60 and the background region 50 can differ in color by a ΔE, which is discussed in more detail below, of at least about 3, if more visual distinctiveness is desired.

Similarly, the second imparted colored region 70 and the background region 50 can differ in color by a ΔE of at least about 1. The first imparted colored region 60 and the second imparted colored region 70 can both differ in color as compared to the background region 50 by a ΔE of at least about 1. The first imparted colored region 60 and the second imparted colored region 70 can be more visually distinguishable if there is a ΔE between the two colors of at least about 3.

As shown in FIG. 1, the second imparted colored region 70 can be laterally more extensive in a direction orthogonally away from the longitudinal centerline L than the first imparted colored region 60. The second imparted colored region 70 can substantially surround the first imparted colored region 60. Manufacturing lines capable of producing current market absorbent articles may already be configured to print a relatively narrow first imparted colored region 60. For instance, some manufacturing lines might employ an inkjet printing apparatus having a cartridge width, as measured in the cross-direction of the manufacturing line, of about 30 mm. Manufacturers that desire to deploy visual signals that are wider in the cross-direction can add an additional component to the manufacturing line that creates a second imparted colored region 70 on a second layer 22, the second imparted colored region 70 being laterally more extensive than the first imparted colored region 60, yet still retain the relatively inexpensive apparatus that may have already been proven to provide a narrower first imparted colored region 60 of sufficient quality and at a sufficient speed. The second layer 22 can be fed into the manufacturing process independently and subsequently combined with the absorbent article 5 in a suitable fashion so as to result in the first layer 20 and second layer 22, and imparted colored regions thereon, combining to produce a combined visual impression, such as the visual impression of depth or increased thickness of the absorbent article 5.

The second imparted colored region 70 can be designed so as to be visually complementary to the first imparted colored region 60 and be presented to the viewer over a wider/more extensive portion of the body facing surface 10. It is thought that by having the second imparted colored region 70 on a different layer of material than the first imparted colored region 60 that a richer visual impression can be created on the absorbent article 5. For instance, since the first imparted colored region 60 and second imparted colored region 70 are on different layers of materials, when viewed, at least one of the colored regions will be viewed through the layer comprising the other colored region. A colored region viewed through another layer material can have a significantly different visual impression in terms of softness/diffuseness of the image, somewhat like the difference between a matte finished photograph versus a gloss finished photograph or the way an undergarment looks beneath a sheer article of clothing. Further, having the second imparted colored region 70 on a different layer of material than the first imparted colored region 60 may be more cost effective than retooling the manufacturing line to print a relatively wide second imparted colored region 70 and first imparted colored region 60 on a single substrate because the approach and equipment for providing the first imparted colored region 60 can continue to be used.

Further, if the first imparted colored region 60 is provided by inkjet printing, the design of the first imparted colored region 60 can be easily changed so that absorbent articles 5 within a single package or different packages can have different designs for the first imparted colored region 60. The second imparted colored region 70 might be provided by a contact printing apparatus that cannot be easily altered. Thus, the second imparted colored region 70 can be a constant design recognizable by consumers as being a product from a particular brand or of a particular quality. Such arrangements can be achieved without altering the portion of the manufacturing line that is used to produce relatively narrow first imparted colored region 60 on a single layer.

A second imparted colored region 70 that is laterally more extensive than the first imparted colored region 60 can also provide the impression to the wearer that such laterally more extensive portions of the absorbent article 5 are capable of acquiring and retaining fluid. For instance, if the second imparted colored region 70 extends across a substantial portion of the absorbent article 5 in the cross-direction CD, viewers of the absorbent article 5 may interpret the second imparted colored region 70 as providing a barrier to fluid flow beyond such second imparted colored region 70 or a boundary beyond which the wearer should not expect fluid to pass as the fluid travels in the machine-direction MD of the absorbent article 5.

Colored regions of varying width imparted on different layers of materials may also offer a wider array of design choices to designers for creating the impression of depth in the absorbent articles 5 and communicating various functions of portions of absorbent article 5, such portions of the absorbent article 5 that might act or be perceived to act as a barrier to flow of liquids.

The first imparted colored region 60 can be coincident with the centroid 40. The centroid 40, being the in-plane center of mass of the absorbent article 5, might be associated by the user as being the location of the absorbent article 5 that should be proximal her vaginal opening or urethra. Designs in which the first imparted colored region 60 is symmetric about the longitudinal centerline may provide for a more pleasing impression of the absorbent article 5 than designs in which the first imparted colored region 60 is not symmetric with respect to the longitudinal centerline L.

As shown in FIG. 1, the first imparted colored region 60 and second imparted colored region 70 can be spaced apart from one another along the longitudinal centerline. By spacing apart the first imparted colored region 60 and second imparted colored region 70, it is believed that improper phasing of the first layer 20 and second layer 22 that might occur when the two layers are brought together or in registration with one another during manufacture might not be so apparent to the consumer because it might be difficult to perceive relatively small differences from one pad to another pad of a gap between the first imparted colored region 60 and second imparted colored region 70. The first imparted colored region 60 and second imparted colored region 70 can be separated from one another by the background region 50.

As shown in FIG. 1, the absorbent article has a periphery 110. The background region 50 can be between the second imparted colored region 70 and the periphery 110. Such an arrangement is thought to provide for an improved visual impression in that the periphery 110 has a clean line that is not interrupted by colored regions of the absorbent article 10. For the same reason, the first imparted colored region 60 and second imparted colored region 70 can be substantially surrounded by the background region 50. For instance, less than 25% of the periphery 110 can be interrupted by the second imparted colored region 70 or first imparted colored region 60 or the combination of the first imparted colored region 60 and second imparted colored region 70. The first imparted colored region 60 can be surrounded by the background region 50.

The first imparted colored region 60, as shown in FIG. 1, can be a substantially elongated shape. Without being bound by theory, it is believed that substantially elongated shapes that are aligned with or on the longitudinal centerline L may make the absorbent article 5 look as if the absorbent article 5 is slim as compared to an absorbent article 5 devoid of such an elongated shape. A consumer might associate such an impression with a belief that the apparently narrow absorbent article 5 will fit comfortably in the crotch of her panty. The first imparted colored region 60 can have a width less than about 50% of the maximum distance between portions of the periphery 110 coincident with the transverse centerline T. Ovals and generally rectangular shaped shapes are examples of substantially elongated shapes. To provide for more visually coherent designs, the first imparted colored region 60 and second imparted colored region 70 can be within a CIELab color space volume of less than about 200. CIELab color space volume is discussed in more detail below. With such an approach, the colors of the first imparted colored region 60 and second imparted colored region 70 do not differ substantially to the eye of most viewers and viewers might perceive the colors to be the same or shades or subtle variations of the same color. Subtle variations in color are thought to be pleasing to the eye, much like sample paint chips having slightly varying colors found in home decoration stores that can be pleasurable and interesting to view. If less distinctiveness between the first imparted colored region 60 and second imparted colored region 70 is desired, the first imparted colored region 60 and second imparted colored region 70 can be within a CIELab color space volume of less than about 50.

The second imparted colored region 70 can be substantially arcuate shaped. Arcuate shaped second imparted colored regions 70 are thought to be perceived by consumers as barriers to flow of liquid in the absorbent article or as providing an indication to a consumer that she may not want fluid to pass beyond such a colored region or that once such fluid flow has occurred she may want to be prepared to wear a fresh product in the near future.

Arcuate shapes include, but are not limited to, shapes generally corresponding to those found on common keyboards including the greater than symbol, parenthesis, circumflex (also referred to as the caret symbol), and bracket as well as generally c-shaped shapes, and slight modifications of any of these previously mentioned shapes. Arcuate shapes, as defined herein, can be generally curved like a letter C or can be more angular such as the symbol <. Thus, arcuate shapes do not necessarily have any particular curvature.

Arcuate shapes can be considered to have an open side and a closed side. The closed side is the side to which the legs 120 of the arcuate shape are oriented and the open side is opposing the closed side. For instance, if the arcuate shape is a closing parenthesis, the closed side is to the left of the parenthesis and the open side is to the right of the parenthesis. In some embodiments, the legs 120 can have free ends 125, which are the ends of the legs 120, if present. The free ends 125 can be located closer to the transverse centerline T than other portions of the second imparted colored region 70. The second imparted colored region 70 can be continuous between the free ends 125. As viewed from the body facing surface 10, the legs 120 can at least partially overlap the first imparted colored region 60, can be spaced apart from the first imparted colored region 60, or can appear to be just be in contact with the first imparted colored region 60. As viewed from the body facing surface 10, the legs 120 can at least partially overlap, be spaced apart from, or just in contact with another colored region. Without being bound by theory, it is thought that arcuate shapes having the closed side oriented towards the centroid 40 of the absorbent article 5 are perceived by consumers as barriers to flow. Such shapes, sized, dimensioned, and located appropriately between the centroid 40 of the absorbent article 5 and the periphery 110 can indicate to the wearer the boundaries of where she should expect staining on the absorbent article 5 under normal usage conditions. The second imparted colored region 70 can be symmetric about the longitudinal centerline L.

The first layer 20 can be a topsheet. The first layer 20 can be a fluid pervious polymer film or a nonwoven material. The first layer 20 can be a secondary topsheet or insert, for instance an intermediate layer that is between the material in contact with the wearer's body when worn and the absorbent core 90 that is designed to collect and retain fluid. The first layer 20 can be an absorbent core. The first layer 20 can be a fibrous nonwoven wherein fibers from the nonwoven protrude through the second layer 22. Fibers from the nonwoven protruding through the second layer 22 can be provided by needle punching or other suitable method for moving the fibers of one web through another web such as disclosed in U.S. Pat. No. 7,410,683.

The second layer 22 can be a topsheet. The second layer 22 can be a fluid pervious polymer film, a nonwoven material, or another suitable fluid pervious material. The second layer 22 can be a secondary topsheet or insert, for instance an intermediate layer that is between the material in contact with the wearer's body, such as the topsheet, when worn and the absorbent core 90 that is designed to collect and retain fluid. The second layer 22 can be an absorbent core.

An absorbent article 5, as described in herein, can be fabricated by providing the first layer 20 with a first imparted colored region 60 coincident with the longitudinal centerline L. The first imparted colored region 60 can be provided by a first coloration technique. The second layer 22 can be provided with a second imparted colored region 70 that is laterally more extensive in a direction orthogonally away from the longitudinal centerline L than the first imparted colored region 60, the second imparted colored region 70 extending across the longitudinal centerline L. The second imparted colored region 70 can be provided by a second coloration technique.

Each of the first imparted colored region 60 and second imparted colored region 70 can be provided by a technique selected from the group consisting of ink jet printing, gravure printing, flexographic printing, lithographic printing, screen printing, and combinations thereof. In one embodiment of the method of fabricating, the coloration technique by which the first imparted colored region is colored can differ from the coloration technique by which the second imparted colored region is colored.

Other means of providing for first imparted colored region 60 and second imparted colored region 70 are contemplated, such means being capable of providing a structure wherein the first imparted colored region 60 and second imparted colored region 70 differ in color as compared to the background region 50. Color can be imparted to a region, for instance, by selectively discoloring a portion of a substrate such that the first imparted colored region 60 and second imparted colored region 70 differ in color as compared to the background region 50.

An absorbent article 5 can be fabricated by a method comprising the steps of providing the first layer 20 with a first imparted colored region 60 coincident with said longitudinal centerline, said first imparted colored region provided by a first coloration technique. A second layer 22 can be provided with a second imparted colored region 70 that is laterally more extensive in a direction orthogonally away from the longitudinal centerline L than the first imparted colored region 60. The second imparted colored region 70 can extend across the longitudinal centerline L. The second imparted colored region 70 can be provided by a second coloration technique. The first layer 20 and the second layer 22 can be brought into registration with one another. The resulting absorbent article 5 can comprise a background region 50. The background region 50, the first imparted colored region 60, and the second imparted colored region 70 can be viewable from the body facing surface 10 of the absorbent article 5. The first imparted colored region 60 and second imparted colored region 70 differ in color as compared to the background region 50.

Figure 2:
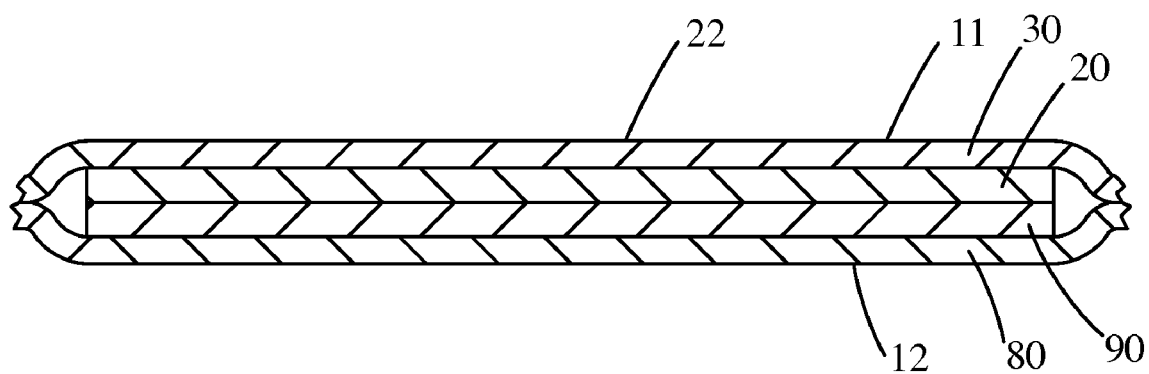
FIG. 2 is a cross-section of the absorbent article illustrated in FIG. 1.

A cross section of the absorbent article 5 illustrated in FIG. 1 is shown in FIG. 2. Each component of the absorbent article 5 can be considered to have a body facing side 11 and a garment facing side 12. The body facing side 11 being oriented towards the wearer's body when the absorbent article is in-use and the garment facing side 12 opposing the body facing side 11.

Figure 3:
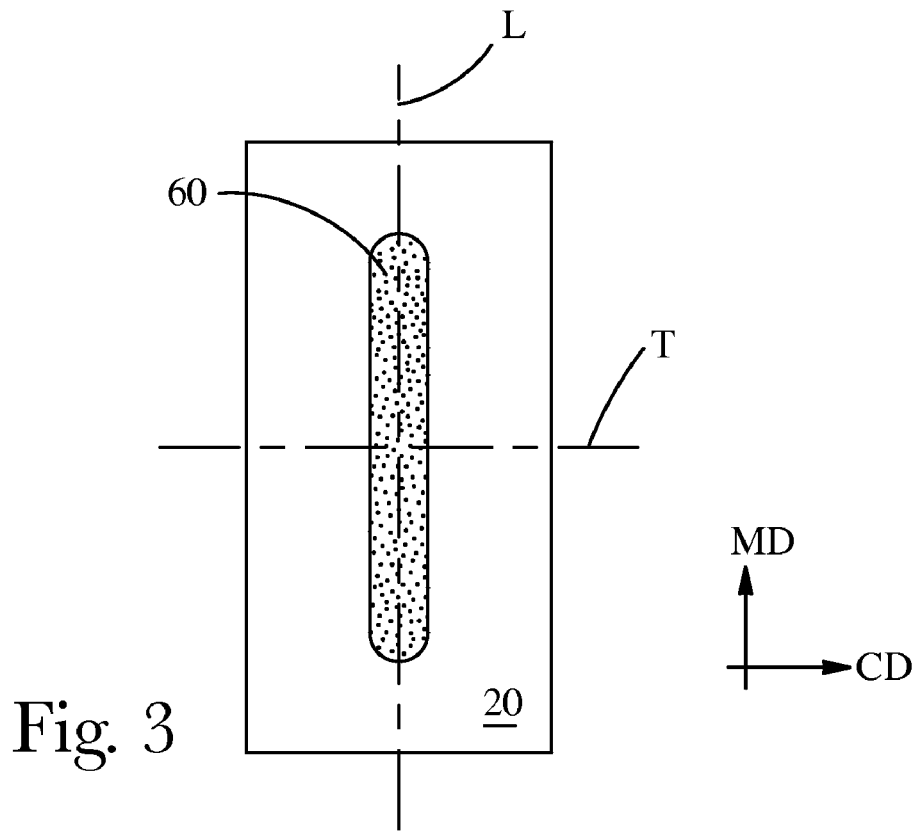
FIG. 3 is a schematic of the first layer of the absorbent article of FIG. 1.
Figure 4:
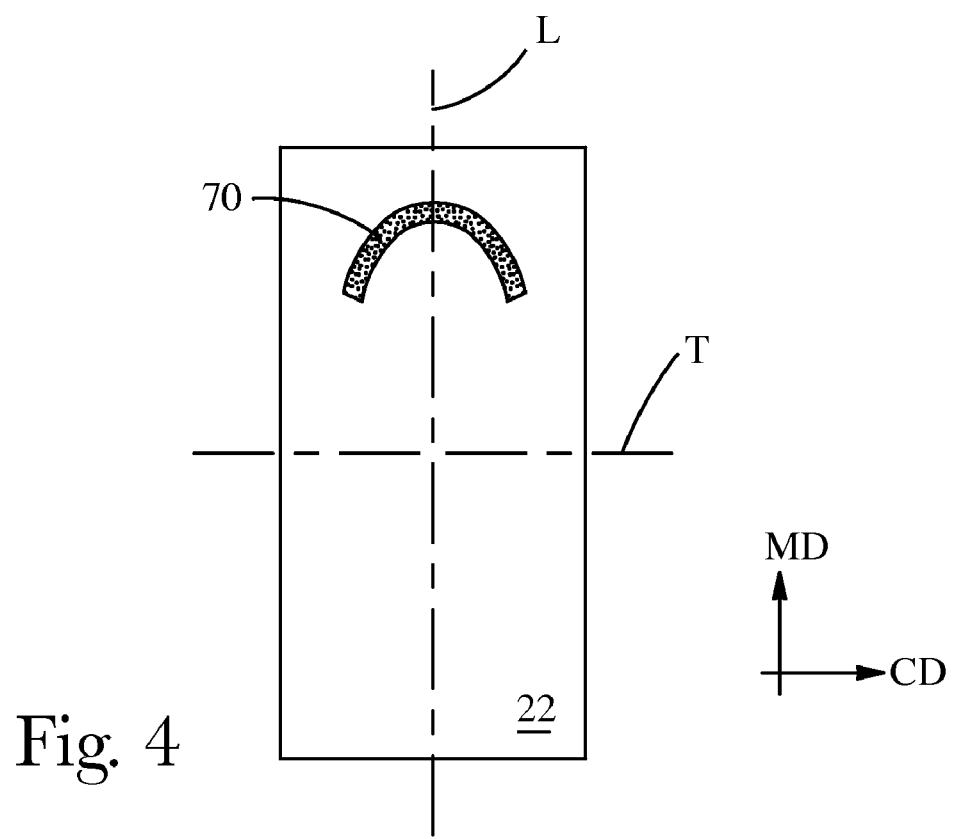
FIG. 4 is a schematic of the second layer of the absorbent article of FIG. 1.

FIG. 3 is a schematic of a first layer 20 of an absorbent article 5 having a first imparted colored region. FIG. 4 is a schematic of a second layer 22 of an absorbent article 5 having a second imparted colored region. The first layer 20 illustrated in FIG. 3 can be registered with the second layer 22 illustrated in FIG. 4 to create an absorbent article 5 having a visual impression similar to that illustrated in FIG. 1.

Figure 5:
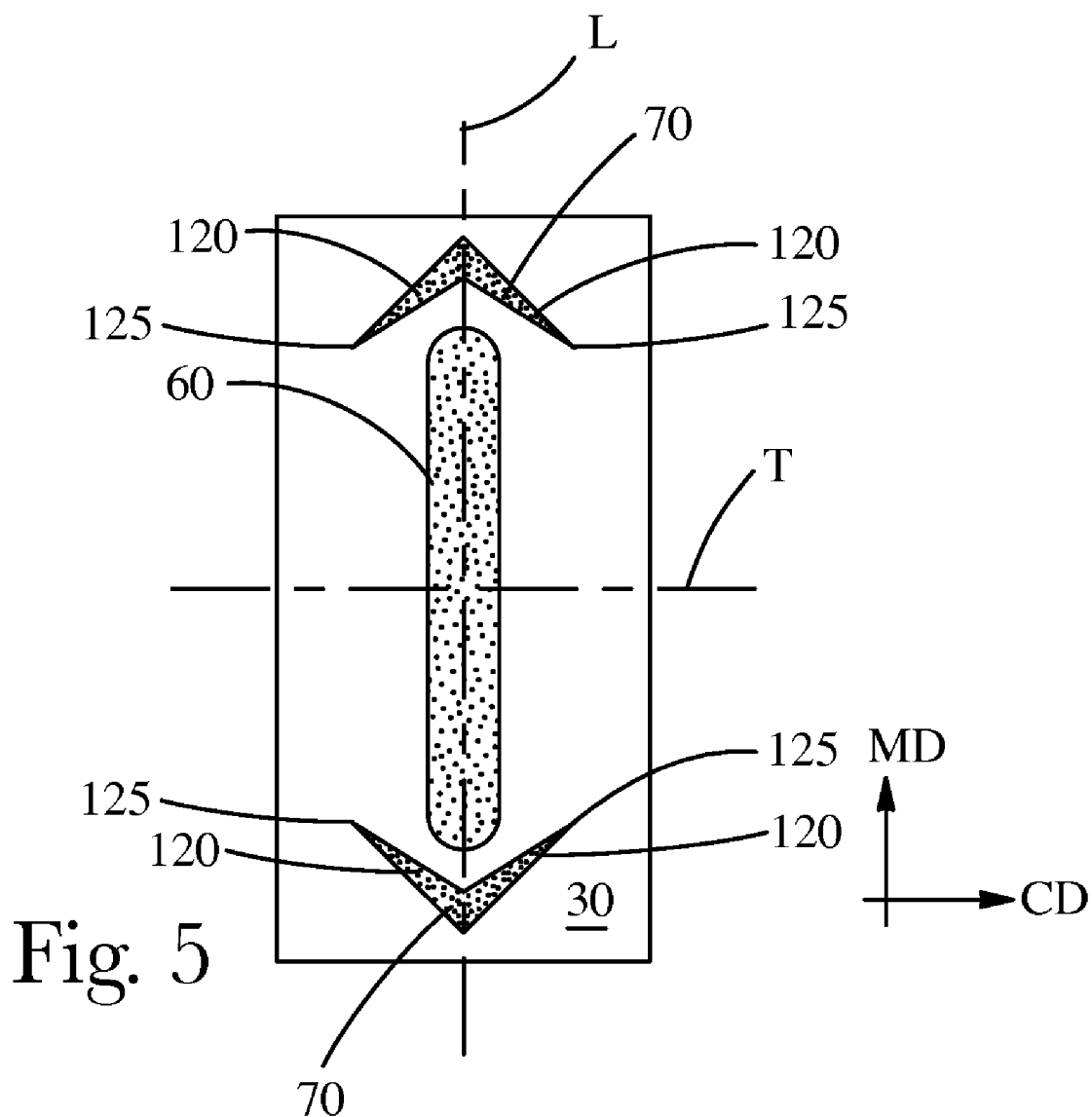
FIG. 5 is a schematic of an absorbent article.

An embodiment of a second imparted colored region 70 is shown in FIG. 5. The second imparted colored region 70 illustrated in FIG. 5, which has free ends 125 that are narrower than other portions of the second imparted colored region 70, may be more effectively perceived by users as delineating a boundary that indicates that a new article 5 may be needed if fluid extends beyond such second imparted colored region 70. As shown in FIG. 5, the absorbent article 5 can comprise two second imparted colored regions 70, wherein the first imparted colored region 60 is between the two second imparted colored regions 70.

The color of the first imparted colored region 60 and second imparted colored region 70 and background region 50 are measured by the reflectance spectrophotometer according to the colors $L^*$, $a^*$, and $b^*$ values. The $L^*$, $a^*$, and $b^*$ values are measured from the body facing surface 10 of the absorbent article 5 inboard of the periphery 110 of the absorbent article 5. The difference in color is calculated using the $L^*$, $a^*$, and $b^*$ values by the formula $\Delta E=[(L^*_{X'}-L^*_{Y})^2+(a^*_{X'}-a^*_{Y})^2+(b^*_{X'}-b^*_{Y})^2]^{1/2}$. Herein, the 'X' in the equation may represent the first imparted colored region 60, the second imparted colored region 70, or the background region 50 and 'Y' may represent the color of another region against which the color of such region is compared. X and Y should not be the same two points of measurement at the same time. In other words, for any particular comparison of the difference in color, the location of X ≠ the location of Y.

Where more than two colors are used, the 'X' and 'Y' values alternately include points of measurement in them also. The key to the $\Delta E$ calculation herein is that the 'X' and 'Y' values should not stem from the same measured point on the viewing surface. In those instances where there is effectively no background region 50 within the confines of the measurement area, the 'X' values should flow from a point different in spatial relationship to the 'Y' values, but within the confines of the absorbent core periphery.

Reflectance color is measured using the Hunter Lab LabScan XE reflectance spectrophotometer obtained from Hunter Associates Laboratory of Reston, Va. An absorbent article 5 is tested at an ambient temperature between 65° F. and 75° F. and a relative humidity between 50% and 80%.

The spectrophotometer is set to the CIELab color scale and with a D65 illumination. The Observer is set at 10° and the Mode is set at 45/0°. Area View is set to 0.125" and Port Size is set to 0.20" for films. The spectrophotometer is calibrated prior to sample analysis utilizing the black glass and white reference tiles supplied from the vendor with the instrument. Calibration is done according to the manufacturer's instructions as set forth in LabScan XE User's Manual, Manual Version 1.1, August 2001, A60-1010-862. If cleaning is required of the reference tiles or samples, only tissues that do not contain embossing, lotion, or brighteners should be used (e.g., PUFFS tissue). Any sample point on the absorbent article containing the imparted color to be analyzed can be selected.

The absorbent article 5 is placed over the sample port of the spectrophotometer with a white clamp disk placed behind the absorbent article 5. The absorbent article 5 is to be in a substantially flat condition and free of wrinkles.

The absorbent article 5 is removed and repositioned so that a minimum of six readings of color of the body facing surface 10 are conducted. If possible (e.g., the size of the imparted color on the element in question does not limit the ability to have six discretely different, non-overlapping sample points), each of the readings is to be performed at a substantially different region on the externally visible surface so that no two sample points overlap. If the size of the imparted colored region requires overlapping of sample points, only six samples should be taken with the sample points selected to minimize overlap between any two sample points. The readings are averaged to yield the reported $L^*$, $a^*$, and $b^*$ values for a specified color on an externally visible surface of an element.

In calculating the CIELab color space volume, V, maximum and minimum $L^*$, $a^*$, and $b^*$ values reported are determined for a particular set of regions to be measured. The maximum and minimum $L^*$, $a^*$, and $b^*$ values reported are used to calculate the CIELab color space volume, V, according to the following formula:

$$V = \frac{4}{3}\left|\frac{\Delta L^*}{2}\right|\left|\frac{\Delta a^*}{2}\right|\left|\frac{\Delta b^*}{2}\right|$$

Within the above formula, ΔL* is the difference in L* values between the two colored regions being compared and is calculated by: $\Delta L^* = L^*_X - L^*_Y$. The Δa* is the difference in a* values between the two colored regions being compared and is calculated by: $\Delta a^* = a^*_X - a^*_Y$. The Δb* is the difference in b* values between the two colored regions being compared and is calculated by: $\Delta b^* = b^*_X - b^*_Y$. The CIELab color space volume can result in a solid substantially ellipsoidal in shape. If ΔL*, Δa*, and Δb* are equal, the solid will be spherical. As used herein, a "solid" refers to the mathematical concept of a three-dimensional figure having length, breadth, and height (or depth). An ellipsoidal volume is preferred to calculate volume because an ellipsoid generally requires the dimensional differences of ΔL*, Δa*, and Δb* to be relatively more uniform than other solids. Furthermore, it is believed that ellipsoidal volumes are more visually acceptable (i.e., less detectable color mismatch by human perception) than spherical volumes.

In some embodiments, the imparted colors of at least two externally visible surfaces of discrete elements will occupy a CIELab color space volume of less than about 200. The externally visible surfaces are analyzed according to the Test Method described below. Upon analysis, the inherent color of an element comprising an externally visible surface will yield L*, a*, and b* coordinates. The CIELab color space volume is then calculated using the formula presented above. The resulting volume can be less than about 200. The resulting volume can be less than about 50.

It should be recognized that the imparted colors of more than two discrete colored regions having a visible surface may occupy the aforementioned CIELab color space volumes. In calculating the CIELab color space volume for more than two elements, the CIELab color space volume is calculated using the maximum and minimum L*, a*, and b* from a set of elements. The maximum color values and minimum color values are used to calculate V according to the formula presented above.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for fabricating an absorbent article having a body facing surface, a garment facing surface, and a periphery, said absorbent article comprising a first layer and a second layer in facing relationship with one another, said absorbent article having a centroid, said absorbent article having a longitudinal centerline and a transverse centerline intersecting said longitudinal centerline at said centroid and orthogonal to said longitudinal centerline, said method comprising the steps of:
   a. providing said first layer with a first imparted colored region coincident with said longitudinal centerline, said first imparted colored region provided by a first coloration technique only on a portion of the first layer;
   b. providing said second layer with a second imparted colored region that is laterally more extensive in a direction orthogonally away from said longitudinal centerline than said first imparted colored region, said second imparted colored region extending across said longitudinal centerline, said second imparted colored region provided by a second coloration technique only on a portion of the second layer; and
   c. registering said first layer and said second layer with one another;
   wherein said absorbent article comprises a background region, wherein said background region, said first imparted colored region, and said second imparted colored region are viewable from said body facing surface, wherein said first imparted colored region and said second imparted colored region differ in color from said background region.

2. The method according to claim 1, wherein said first coloration technique is selected from the group consisting of ink jet printing, gravure printing, flexographic printing, lithographic printing, and screen printing, and combinations thereof and said second coloration technique is selected from the group consisting of ink jet printing, gravure printing, flexographic printing, lithographic printing, screen printing, and combinations thereof.

3. The method according to claim 2, wherein said first coloration technique differs from said second coloration technique.

4. The method according to claim 1, wherein said first imparted colored region, said second imparted colored region, and said background region are measured by a Hunter Reflectance Meter test according to the colors L*, a*, and b*, the L*, a*, and b* values being measured from said body facing surface, wherein said first imparted colored region and said second imparted colored region have a color difference, the color difference being calculated using the L*, a*, and b* values by the formula $\Delta E = [(L^*_X - L^*_Y)^2 + (a^*_X - a^*_Y)^2 + (b^*_X - b^*_Y)^2]^{1/2}$, wherein said ΔE between said first imparted colored region and said background region is at least about 1 and wherein said ΔE between said second imparted colored region and said background region is at least about 1.

5. The method according to claim 1, wherein the first layer and the second layer form a topsheet of the absorbent article.

* * * * *